US012673314B2

(12) United States Patent
Zhang et al.

(10) Patent No.: US 12,673,314 B2
(45) Date of Patent: Jul. 7, 2026

(54) SUPPORTED CATALYST AND METHOD FOR SYNTHESIZING SUCROSE-6-ESTER

(71) Applicant: ANHUI JINHE INDUSTRIAL CO., LTD., Chuzhou City (CN)

(72) Inventors: Zhengsong Zhang, Chuzhou City (CN); Zhijian Yang, Chuzhou City (CN); Jingang Zhao, Chuzhou City (CN); Zhenghua Li, Chuzhou City (CN); Chaohui Chen, Chuzhou City (CN)

(73) Assignee: ANHUI JINHE INDUSTRIAL CO., LTD., Chuzhou City (CN)

( * ) Notice: Subject to any disclaimer, the term of this patent is extended or adjusted under 35 U.S.C. 154(b) by 482 days.

(21) Appl. No.: 18/036,623

(22) PCT Filed: Mar. 24, 2021

(86) PCT No.: PCT/CN2021/082598
§ 371 (c)(1),
(2) Date: May 11, 2023

(87) PCT Pub. No.: WO2022/198478
PCT Pub. Date: Sep. 29, 2022

(65) Prior Publication Data
US 2023/0415126 A1 Dec. 28, 2023

(51) Int. Cl.
*B01J 23/14* (2006.01)
*B01J 31/12* (2006.01)
*C07D 407/12* (2006.01)

(52) U.S. Cl.
CPC ............. *B01J 23/14* (2013.01); *B01J 31/124* (2013.01); *C07D 407/12* (2013.01); *B01J 2231/49* (2013.01); *B01J 2531/42* (2013.01)

(58) Field of Classification Search
CPC . B01J 23/14; B01J 31/06; B01J 31/124; B01J 2231/49; B01J 2531/42; C07D 407/12
See application file for complete search history.

(56) References Cited

U.S. PATENT DOCUMENTS 5,470,969 A 11/1995 Sankey et al.
7,781,610 B2 * 8/2010 Schneider ................ B01J 31/12 560/92

(Continued)

FOREIGN PATENT DOCUMENTS

CN 1714935 A 1/2006
CN 102002078 A 4/2011

(Continued)

OTHER PUBLICATIONS

CNIPA, "Office Action Issued in Chinese Patent Application No. 202180000705.1", Jan. 7, 2022, pp. 3, Published in: CN, All reviewed on English aspects only.

(Continued)

*Primary Examiner* — Richard M Rump
(74) *Attorney, Agent, or Firm* — NOD Law PC

(57) ABSTRACT

Provided are a supported catalyst and a method for synthesizing a sucrose-6-ester. The supported catalyst includes an active functional component and an inorganic carrier, wherein the active functional component is a compound shown in formula (1), wherein n is a natural number greater than or equal to 2; R is an atom linked to a surface of the inorganic carrier; and one or two of $R_1$, $R_2$, and $R_3$ is/are hydrocarbyl, and the rest are independently any one selected from the group consisting of oxygen, hydroxyl, hydrocarbyloxy, and acetoxy.

20 Claims, 1 Drawing Sheet

(56) References Cited

U.S. PATENT DOCUMENTS

| | | | | |
|---|---|---|---|---|
| 9,724,673 | B2 * | 8/2017 | Le Grognec | C07D 257/04 |
| 2014/0206825 | A1 * | 7/2014 | Le Grognec | C08F 8/42 548/252 |

FOREIGN PATENT DOCUMENTS

| | | | |
|---|---|---|---|
| CN | 111205340 | A | 5/2020 |
| CN | 112218874 | A | 1/2021 |
| WO | 2022198478 | A1 | 9/2022 |

OTHER PUBLICATIONS

Wu Hongying et al.: "Recent Advances in Synthesis of Sweetener Sucralose [J", Chemical Industry and Engineering Progress, vol. 35, No. 1, 2016, pp. 227-238.

Zhang Zhaohui: "Guangxi Nanning Cassava Technology Development Center, Chemical Derivatives from Sucrose [J", Advances in Fine Petrochemicals, vol. 1, No. 6, 2000, pp. 8-13.

International Bureau, International Application Status Report for PCT/CN2021/082598, Dec. 16, 2022, p. 1.

* cited by examiner

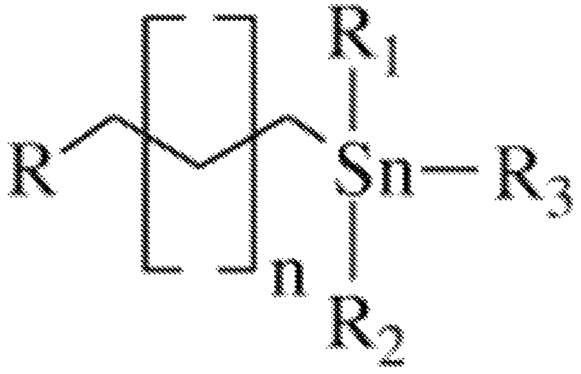

SUPPORTED CATALYST AND METHOD FOR SYNTHESIZING SUCROSE-6-ESTER

CLAIM OF PRIORITY UNDER 35 U.S.C. § 119

The present Application for Patent is a 35 U.S.C. 371 application of International Application No. PCT/CN2021/082598 entitled "SUPPORTED CATALYST AND METHOD FOR SYNTHESIZING SUCROSE-6-ESTER" filed Mar. 24, 2021, pending, and assigned to the assignee hereof and hereby expressly incorporated by reference herein.

TECHNICAL FIELD

The present disclosure belongs to the technical field of fine chemicals, and specifically relates to a supported catalyst and a method for synthesizing a sucrose-6-ester.

BACKGROUND

Sucrose-6-carboxylate (namely, a sucrose-6-ester) is an important chemical product and intermediate (Zhang Zhaohui, Guangxi Nanning Cassava Technology Development Center, Chemical Derivatives from Sucrose [J]. Advances in Fine Petrochemicals, 2000, 1 (6): 8-13.), and is widely used in industry. For example, sucrose-6-fatty acid esters are a kind of polyol-nonionic surfactant with excellent emulsifying properties and are widely used in industries, such as food, medicine, and cosmetics; for example, sucrose rosin acid ester is also an excellent emulsifying agent; and sucrose-6-acetate is not only a raw material for the synthesis of sucrose-6-fatty acid ester and sucrose acetate isobutyrate (SAIB) but also an important intermediate for the synthesis of sucralose (Wu Hongying, College of Chemical and Biological Engineering, Zhejiang University, Wu Hongying, et al. Recent Advances in Synthesis of Sweetener Sucralose [J]. Chemical Industry and Engineering Progress, 2016, 35 (1): 227-238.). Therefore, the synthesis of sucrose-6-ester has important practical values.

At present, the mono-group protection method is the most widely used technology for synthesizing a sucrose-6-ester. The mono-group protection method comprises: an organo-tin compound and sucrose are subjected to dehydration in a polar solvent to form a sucrose organic tin ester solution, and then the sucrose organic tin ester solution and a carboxylic anhydride (an acylating agent) are subjected to a highly-selective reaction to obtain sucrose-6-carboxylate.

The mono-group protection method has mild conditions, high selectivity, high yield, catalyst circulation, and less waste, so it has become the main process for producing sucrose-6-esters. However, the mono-group protection method still has many shortcomings. For example, the mono-group protection method needs to be conducted with a two-step reaction process, wherein in step 1, a sucrose organic tin ester is prepared; and in step 2, the sucrose organic tin ester reacts with a carboxylic anhydride after being cooled to obtain a sucrose-6-carboxylate, and the residual carboxylic anhydride is subsequently quenched with water. The organic tin is extracted and recovered with a solvent, and then concentrated to a constant volume for the next reaction or application. In the above process, the separation of the organo-tin catalyst is difficult and requires quenching with water, extracting, and recovering. In addition, because the organo-tin compound is distributed in a light phase during extraction and recovery, it is difficult to completely recover the organo-tin compound, such that 1% to 5% of the catalyst will be lost due to material entrainment during the reaction process, which makes it necessary to supplement new organic tin catalyst for the next production and causes an adverse effect on the subsequent chlorination reaction due to the entrained catalyst. The overall process operation, labor energy consumption, and production cost of the mono-group protection method are relatively large problems. In addition, because carboxylic anhydride, especially acetic anhydride, is a controlled product, the preparation of sucrose-6-acetate by the above method will be restricted in many aspects.

It should be noted that the statements herein merely provide background information related to the present disclosure and do not necessarily constitute the prior art.

SUMMARY

In view of the above problems, the present disclosure provides a supported catalyst and a method for synthesizing a sucrose-6-ester which makes it possible to overcome the above problems or at least partially solve the above problems.

According to one aspect of the present disclosure, provided is a supported catalyst for catalyzing a transesterification reaction between sucrose and carboxylate, comprising an active functional component and an inorganic carrier, wherein the active functional component is a compound shown in formula (1):

formula (1)

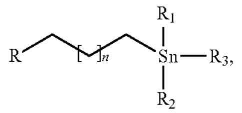

wherein n is a natural number greater than or equal to 2;
- R is an atom linked to a surface of the inorganic carrier; and one or two of $R_1$, $R_2$, and $R_3$ is/are hydrocarbyl, and the rest are independently any one selected from the group consisting of oxygen, hydroxyl, hydrocarbyloxy, and acetoxy.

In some embodiments, in the supported catalyst, R is any one selected from the group consisting of silicon, oxygen, nitrogen, sulfur, and phosphorus.

In some embodiments, in the supported catalyst, hydrocarbyl is selected from the group consisting of alkyl, cycloalkyl, aryl, and aralkyl, and preferably alkyl. In some embodiments, hydrocarbyl is n-butyl.

In some embodiments, in the supported catalyst, hydrocarbyloxy is selected from the group consisting of alkoxy and phenoxy. In some embodiments, hydrocarbyloxy is selected from the group consisting of methoxy, ethoxy, n-propoxy, n-butoxy, n-pentoxy, and n-hexoxy. In some other embodiments, hydrocarbyloxy is methoxy.

In some embodiments, in the supported catalyst, the inorganic carrier is one or a mixture of two or more selected from the group consisting of silicon dioxide, titanium dioxide, activated carbon, and aluminum oxide. In some embodiments, the inorganic carrier is silicon dioxide.

In some embodiments, in the supported catalyst, the inorganic carrier has a specific surface area (SSA) of greater than 10 $m^2/g$. In some embodiments, the inorganic carrier has an SSA of greater than 30 $m^2/g$, In some other embodiments, the inorganic carrier has an SSA of greater than 100 $m^2/g$.

In some embodiments, in the supported catalyst, the active functional component accounts for 1 ppm to 40% of a weight of the inorganic carrier, and preferably 1,000 ppm to 10%.

According to another aspect of the present disclosure, provided is a method for synthesizing a sucrose-6-ester, comprising: using the supported catalyst described above to catalyze a transesterification reaction between sucrose and a low-alcohol carboxylate to obtain the sucrose-6-ester.

In some embodiments, the method comprises:

sucrose dissolution: heating and dissolving sucrose in a polar aprotic solvent to obtain a sucrose solution;

catalyst addition: adding the supported catalyst described above into the sucrose solution to obtain a reaction suspension; and transesterification reaction: adding a low-alcohol carboxylate to the reaction suspension, and conducting a dehydration and dealcoholization treatment to promote a transesterification reaction to obtain a reaction mixed solution having the sucrose-6-ester as a main product.

In some embodiments, the method further comprises:

post-treatment: filtering the reaction mixed solution to separate the supported catalyst to obtain a sucrose-6-ester mother liquor.

In some embodiments, in the method, the low-alcohol carboxylate is one or more selected from the group consisting of methyl esters, ethyl esters, propyl esters, isopropyl esters, n-butyl esters, isobutyl esters, tert-butyl esters, and phenylmethyl esters of stearic acid, benzoic acid, acetic acid, butyric acid, and lauric acid. In some embodiments, the low-alcohol carboxylate is one or more selected from the group consisting of methyl stearate, ethyl acetate, and methyl benzoate.

In some embodiments, in the method, the polar aprotic solvent is one or more selected from the group consisting of dimethyl sulfoxide (DMSO), acetonitrile, 1,4-dioxane, methyl ethyl ketone (MEK), methyl isobutyl ketone (MIBK), nitromethane, nitroethane, cyclohexanone, N-methylpyrrolidone (NMP), NMP, N,N-dimethylacetamide (DMA), hexamethylphosphoramide (HMPA), and N,N-dimethylformamide (DMF). In some embodiments, the polar aprotic solvent is acetonitrile and/or DMF.

In some embodiments, in the method, a ratio of a volume of the polar aprotic solvent to a mass of sucrose is in a range of 2-50 mg/L. In some embodiments, the ratio of a volume of the polar aprotic solvent to a mass of sucrose is in a range of 4-20 mg/L. In some other embodiments, the ratio of a volume of the polar aprotic solvent to a mass of sucrose is in a range of 6-10 mg/L.

Based on the active functional component, a molar ratio of the supported catalyst to sucrose is in a range of 0.01 to 2. In some embodiments, the molar ratio of the supported catalyst to sucrose is in a range of 0.05 to 0.5.

A volume of the low-alcohol carboxylate is less than 30% of the volume of the polar aprotic solvent. In some embodiments, the volume of the low-alcohol carboxylate is less than 20% of the volume of the polar aprotic solvent. In some other embodiments, the volume of the low-alcohol carboxylate is less than 15% of the volume of the polar aprotic solvent.

In some embodiments, in the method, the dehydration and dealcoholization treatment is conducted by distillation of an additional polar aprotic solvent or low-alcohol carboxylate added to the reaction suspension.

In some embodiments, in the method, the distillation is performed as follows: the distillation is conducted at a temperature of 40° C. to 100° C. In some embodiments, the distillation is conducted at a temperature of 60° C. to 80° C. The distillation is conducted under a pressure of 0.01 kPa to 100 kPa. In some embodiments, the distillation is conducted under a pressure of 0.5 kPa to 90 kPa. The distillation is conducted for 1 min to 12 h. In some embodiments, the distillation is conducted for 30 min to 4 h.

In some embodiments, in the method, the transesterification reaction is conducted in a kettle-type reactor or a continuous countercurrent reaction distillation tower.

In summary, the present disclosure provides a supported catalyst, wherein an active component of an organic tin compound shown in formula (1) is supported on an inorganic carrier to obtain the supported catalyst. The supported catalyst can highly selectively catalyze a transesterification reaction between sucrose and a low-alcohol carboxylate to obtain a sucrose-6-ester. After the reaction is completed, the supported catalyst can be recovered almost completely through filtration with almost no loss. In this way, there is no need to add a new catalyst for the next production run, and there is no entrained catalyst in the product, such that the subsequent reaction will not be adversely affected. The use of the low-alcohol carboxylate as the raw material can avoid the control restrictions on the use of carboxylic anhydride in the prior art, and can also avoid recovering the catalyst after the quenching of the residual acylating agent with water and the subsequent complex dehydration processes, which makes the overall process simple and easy to implement and has significant economic benefits in terms of manpower, equipment, and energy consumption.

The above description is merely a summary of the technical solutions of the present disclosure. In order to allow the technical means of the present disclosure to be understood clearly and implemented in accordance with the content of the specification and allow the above and other objectives, features, and advantages of the present disclosure to be obvious and easy to understand, specific implementations of the present disclosure are described below.

BRIEF DESCRIPTION OF THE DRAWINGS

The present disclosure will be explained in detail with reference to the accompanying drawings.

FIG. 1 is a formula for an active functional component of an embodiment of a supported catalyst for catalyzing a transesterification reaction between sucrose and carboxylate.

DETAILED DESCRIPTION OF THE EMBODIMENTS

Exemplary embodiments of the present disclosure will be described in detail below with reference to the drawing. Although the drawing shows an exemplary embodiment of the present disclosure, it should be understood that the present disclosure may be implemented in various forms and should not be limited to the embodiments described herein. Instead, these embodiments are provided to enable a more thorough understanding of the present disclosure, and the scope of the present disclosure can be fully conveyed to those skilled in the art.

The concept of the present disclosure is as follows:

In view of the problems faced by the mono-group protection method for producing sucrose-6-esters in the prior art that there is a process load. The liquid organic tin catalyst is difficult to recover and will adversely affect the subsequent production step. In addition, the raw material carboxylic anhydride is strictly controlled. The present disclosure provides a solid supported catalyst, wherein an organic tin active component is supported on an inorganic carrier to obtain a catalyst. The catalyst can efficiently catalyze a transesterification reaction between sucrose and a low-alcohol carboxylate to obtain a sucrose-6-ester. The catalyst is easy to recover and the use of a carboxylic anhydride is avoided.

In some embodiments of the present disclosure, provided is a supported catalyst for catalyzing a transesterification reaction between sucrose and carboxylate, comprising an active functional component and an inorganic carrier, wherein the active functional component is a compound shown in formula (1):

formula (1)

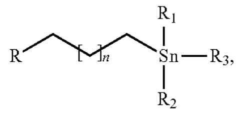

wherein n is a natural number greater than or equal to 2;

R is an atom linked to a surface of the inorganic carrier; and one or two of $R_1$, $R_2$, and $R_3$ is/are hydrocarbyl, and the rest are independently any one selected from the group consisting of oxygen, hydroxyl, hydrocarbyloxy, and acetoxy.

Specifically, in some embodiments of the present application, in the supported catalyst, R is an atom linked to a surface of the inorganic carrier, and may be, but is not limited to, any one selected from the group consisting of silicon, oxygen, nitrogen, sulfur, and phosphorus.

In some embodiments of the present application, the inorganic carrier may be, but is not limited to, one or a mixture of two or more selected from the group consisting of silicon dioxide, titanium dioxide, activated carbon, and aluminum oxide. In some embodiments, the inorganic carrier is silicon dioxide.

There is usually an atom or a group that can form a covalent bond on the surface of the inorganic carrier. For example, hydroxyl on the surface of silicon dioxide or oxygen left after hydrogen in hydroxyl broken can form a covalent bond with an atom represented by R, such that the active functional component is supported on the surface of the inorganic carrier or in the pore of the inorganic carrier. It should be noted that the combination of the organic tin active functional component with the inorganic carrier is not limited to the covalent bond form described above. The above is only used as an illustrative example to make those skilled in the art easily understand the present disclosure.

Therefore, the supported catalyst described above can be prepared by fixing the organic tin active functional component shown in formula (1) on the surface of the inorganic carrier by forming chemical bond. In the present disclosure, there is no limitation on the preparation method of the supported catalyst, and those skilled in the art can refer to the prior art. For example, the organic tin catalyst with a silicon-coupled atom formed on the surface of silicon oxide is prepared as follows: a carrier with a silicon oxide surface (which can be silicon oxide or another carrier coated with silicon oxide) is prepared into a suspension with a solvent, then an organic tin active functional component with an organosiloxane or chlorosilane structure is added to the suspension, and a reaction is conducted at a specified temperature such that organosiloxane or chlorosilane structure is covalently linked to the surface of silicon oxide to obtain a catalyst with the organic tin active functional component. For example, a supported catalyst with a nitrogen-coupled atom formed on an aminoated surface is prepared as follows: a carrier with an aminoated surface is suspended in a solvent to obtain a suspension, then the halogen-substituted organic tin active functional component is added to the suspension, and a reaction is conducted at a specified temperature such that amino and the halogenated hydrocarbon structure are covalently linked to obtain a catalyst with the organic tin active functional component.

Specifically, in some embodiments of the present disclosure, in the supported catalyst, hydrocarbyl may be selected from the group consisting of alkyl, cycloalkyl, aryl, and aralkyl. In some embodiments, hydrocarbyl may be alkyl. In some other embodiments, hydrocarbyl may be n-butyl.

Wherein alkyl may be but not limited to, methyl, ethyl, propyl, isopropyl, butyl, isobutyl, tert-butyl, pentyl, isopentyl, neopentyl, n-hexyl, branched hexyl, n-heptane, branched heptane, n-octane, or branched octane.

Cycloalkyl may be but not limited to, cyclopropyl, cyclobutyl, cyclopentyl, cyclohexyl, monosubstituted cyclopropyl, such as methylcyclopropyl and ethylcyclopropyl; disubstituted cyclopropyl, such as dimethylcyclopropyl and methylethylcyclopropyl; monosubstituted cyclobutyl, disubstituted cyclobutyl, and trisubstituted cyclobutyl, such as trimethylcyclobutyl; monosubstituted cyclopentyl, disubstituted cyclopentyl, and trisubstituted cyclopentyl, such as methylethylcyclopentyl; and monosubstituted cyclohexyl and disubstituted cyclohexyl, such as methylcyclohexyl. Cycloalkyl may also be but not limited to, cyclopropenyl, cyclobutenyl, cyclopentenyl, cyclohexenyl, cyclopropynyl, cyclobutynyl, cyclopentynyl, cyclohexynyl, monosubstituted cyclopropenyl and disubstituted cyclopropenyl, such as methylcyclopropenyl; monosubstituted cyclobutenyl, disubstituted cyclobutenyl, and trisubstituted cyclobutenyl, such as dimethylcyclobutenyl; monosubstituted cyclopentenyl, disubstituted cyclopentenyl, and trisubstituted cyclopentenyl, such as methylethylcyclopentenyl; monosubstituted cyclohexenyl and disubstituted cyclohexenyl, such as methylcyclohexenyl; monosubstituted cyclopropynyl and disubstituted cyclopropynyl, such as dimethylcyclopropynyl; monosubstituted cyclobutynyl, disubstituted cyclobutynyl, and trisubstituted cyclobutynyl, such as ethylcyclobutynyl; monosubstituted cyclopentynyl, disubstituted cyclopentynyl, and trisubstituted cyclopentynyl, such as methylethylcyclopentynyl; and monosubstituted cyclohexynyl and disubstituted cyclohexynyl, such as methylcyclohexynyl.

Aryl may be but not limited to, phenyl, monosubstituted phenyl, disubstituted phenyl, trisubstituted phenyl, tetrasubstituted phenyl, pentasubstituted phenyl, and hexasubstituted phenyl, such as methylethylphenyl, benzocyclobutyl, and benzocyclopentyl.

Aralkyl may be but not limited to, monosubstituted phenyl, disubstituted phenyl, trisubstituted phenyl, tetrasubstituted phenyl, pentasubstituted phenyl, and hexasubstituted phenyl, such as methylethylphenyl, benzocyclobutyl, and benzocyclopentyl.

Specifically, in some embodiments of the present disclosure, in the supported catalyst, hydrocarbyloxy may be but not limited to selected from the group consisting of alkoxy and phenoxy, wherein alkoxy may be but not limited to selected from the group consisting of methoxy, ethoxy, n-propoxy, n-butoxy, n-pentoxy, and n-hexoxy. In some other embodiments, hydrocarbyloxy is methoxy.

In some embodiments of the present disclosure, in the supported catalyst, the inorganic carrier has an SSA of greater than 10 $m^2/g$. In some embodiments, the inorganic carrier has an SSA of greater than 30 $m^2/g$. In some other embodiments, the inorganic carrier has an SSA of greater than 100 $m^2/g$.

SSA refers to a total area per unit mass of a material. In the present disclosure, the SSA of the inorganic carrier may be measured by any method in the prior art, such as a continuous flow method (namely, a dynamic method) and a static capacity method. When the inorganic carrier is used as a catalyst, a large SSA usually enables obtaining a prominent technical effect because it can provide many sites that can be linked to an R atom. In the present disclosure, the inorganic carrier may have, but is not limited to, an SSA of greater than 10 $mm^2/g$. In some embodiments, the inorganic carrier may have, but is not limited to, an SSA of greater than 30 $mm^2/g$ In some other embodiments, the inorganic carrier may have, but is not limited to, an SSA of greater than 100 $mm^2/g$.

In some embodiments of the present disclosure, in the supported catalyst, the active functional component accounts for 1 ppm to 40% of a weight of the inorganic carrier. In some other embodiments, the active functional component accounts for 1,000 ppm to 10% of a weight of the inorganic carrier.

Through a variety of experiments, a desired proportion of the active functional component and the inorganic carrier were determined. In some embodiments, the active functional component accounts for 1 ppm to 40% of a weight of the inorganic carrier. In some other embodiments, the active functional component accounts for 1,000 ppm to 10% of a weight of the inorganic carrier. If the active functional component accounts for less than 1 ppm of the weight of the inorganic carrier, the content of the active functional component is too small to effectively catalyze the transesterification reaction between sucrose and a low-alcohol carboxylate. On the one hand, the reaction selectivity is low, resulting in the production of a variety of esters other than the 6-substituted product. On the other hand, the reaction yield is low. If the weight of the active functional component accounts for less than 40% of the weight of the inorganic carrier, the content of the active functional component is too much, and the inorganic carrier cannot provide enough active sites for supporting the active functional component, such that a large amount of the active functional component cannot be effectively supported on the surface of the catalyst in the process of catalyst preparation, resulting in a waste of the active functional component without bringing other beneficial effects.

According to some embodiments of the present disclosure, the present disclosure also provides a method for synthesizing a sucrose-6-ester, comprising: using the supported catalyst described above to catalyze a transesterification reaction between sucrose and a low-alcohol carboxylate to obtain the sucrose-6-ester.

In the prior art, a di-tin or multi-tin organic oxide, such as di(alkyl)tin oxide, 1,3-bis(oxyl)-1,1,3,3-tetra-(alkyl) distannoxane, 1,3-diacyloxy-1,1,3,3-tetra-(alkyl) distannoxane, 1-acyloxy-1,1,3,3-tetra-(alkyl) distannoxane, and diacyl-dialkyl-tin, is usually used to react with sucrose to obtain an organic tin ester solution, and then further react with an acid anhydride to obtain a sucrose-6-ester. Due to the structure of di-tin, the organo-tin compound is distributed in a light phase. It is difficult to completely recover the organo-tin compound. As a result, 1% to 5% of the catalyst will be lost each time due to material entrainment during the reaction process, which makes it necessary to supplement the organo-tin compound for the next production and causes an adverse effect on the subsequent chlorination reaction due to the entrained catalyst.

In the present disclosure, an active component of an organic monotin compound shown in formula (1) is supported on an inorganic carrier to obtain the supported catalyst. The supported catalyst can highly selectively catalyze a transesterification reaction between sucrose and a low-alcohol carboxylate to obtain a sucrose-6-ester. After the reaction is completed, the supported catalyst can be recovered almost completely through filtration with almost no loss. In this way, there is no need to add a new catalyst for the next production run, and there is no entrained catalyst in the product, such that the subsequent reaction will not be adversely affected. The use of the low-alcohol carboxylate as the reaction raw material can avoid the control restrictions on the use of carboxylic anhydride in the prior art, and can also avoid recovering the catalyst after the quenching of the residual acylating agent with water and the subsequent complex dehydration processes, which makes the overall process simple and easy to implement and has significant economic benefits in terms of manpower, equipment, and energy consumption. Therefore, the method provided in the present disclosure can greatly improve production efficiency, achieve large-scale operation, increase the operability of the process, simplify the production process to achieve higher automation level, and reduce energy consumption and operation costs, thereby achieving the purpose of large-scale industrial production.

According to some embodiments of the present disclosure, the method at least comprises the following steps:

Sucrose dissolution: Sucrose is heated and dissolved in a polar aprotic solvent to obtain a sucrose solution.

In the present disclosure, there is no limitation on the dissolution temperature and dissolution method of sucrose, as long as sucrose can be completely dissolved. For example, the dissolution temperature may be room temperature to 80° C. The auxiliary means of stirring can also be used to accelerate the dissolution of sucrose to obtain the sucrose solution.

Catalyst addition: The supported catalyst described above is added into the sucrose solution to obtain a reaction suspension.

The supported catalyst described above is added into the sucrose solution. Because the supported catalyst described above is a solid (specifically including but not limited to, granule), after the supported catalyst is added into the sucrose solution, a suspension is obtained. Therefore, in the present disclosure, the transesterification reaction between sucrose and the low-alcohol carboxylate is conducted in a two-phase solution.

Transesterification reaction: a low-alcohol carboxylate is added to the reaction suspension, and a dehydration and dealcoholization treatment is conducted to promote a transesterification reaction to obtain a reaction mixed solution having the sucrose-6-ester as a main product.

The mixture obtained after the reaction between sucrose and the low-alcohol carboxylate comprises a main product sucrose-6-ester, by-products water and low alcohol, and a very small amount of sucrose and the low-alcohol carboxylate that fails to completely react. Therefore, the dehydration and dealcoholization can significantly promote the transesterification reaction to proceed in a forward direction, improve the conversion rate of sucrose, and improve the yield of the sucrose-6-ester.

In some embodiments of the present disclosure, the method further comprises: post-treatment: the reaction mixed solution is filtered to separate the supported catalyst to obtain a sucrose-6-ester mother liquor.

That is, in the present disclosure, because the supported catalyst is solid, when the transesterification reaction is completed, the catalyst can be basically completely separated through simple filtration to obtain the sucrose-6-ester mother liquor that can be directly used for the next reaction. Furthermore, in order to obtain a high-purity sucrose-6-ester solution, the solvent and the unreacted low-alcohol carboxylate in the sucrose-6-ester mother liquor can be distilled through distillation to highly selective obtain a sucrose-6-ester.

In some embodiments of the present disclosure, in the method, the transesterification reaction is conducted in a kettle-type reactor or a continuous countercurrent reaction distillation tower.

In the present disclosure, the transesterification reaction may be conducted in a conventional kettle-type reactor or a continuous countercurrent reaction distillation tower, such as a packed tower, a plate tower, and a thermal spray reactor.

Type and Amount of the Polar Aprotic Solvent

In some embodiments of the present disclosure, there is no limitation on the type of the polar aprotic solvent, and the polar aprotic solvent may be, but is not limited to, one or a mixture of two or more selected from the group consisting of DMSO, acetonitrile, 1,4-dioxane, MEK, MIBK, nitromethane, nitroethane, cyclohexanone, NMP, NMP, DMA, HMPA, and DMF. In some other embodiments, the polar aprotic solvent is acetonitrile and/or DMF.

In some embodiments of the present disclosure, there is no limitation on the amount of the polar aprotic solvent. A ratio of a volume of the polar aprotic solvent to a mass of sucrose may be but not limited to a range of 2-50 mg/L. In some embodiments, the ratio of a volume of the polar aprotic solvent to a mass of sucrose may be a range of 4-20 mg/L. In some other embodiments, the ratio of a volume of the polar aprotic solvent to a mass of sucrose may be a range of 6-10 mg/L.

If the volume amount of the polar aprotic solvent is less than 2 times the mass amount of sucrose, the amount of polar aprotic solvent is too small, and the sucrose cannot be completely dissolved, resulting in a waste of a part of sucrose raw material, and adversely affecting the heat transfer and mass transfer in the subsequent reaction process due to the sucrose existing in a solid form. If the mass amount of the mixed solvent is more than 50 times the mass amount of sucrose, the amount is too much, which causes waste of the raw materials, brings great trouble to the subsequent solvent treatment and even causes excessive energy consumption, increased production costs, reduced efficiency, and environmental pollution.

Amount of the Catalyst

In some embodiments of the present disclosure, there is no limitation on the amount of the catalyst. Based on the active functional component, a molar ratio of the supported catalyst to sucrose may be, but is not limited to, a range of 0.01 to 2. In some embodiments, the molar ratio of the supported catalyst to sucrose may be, but is not limited to, a range of 0.05 to 0.5.

Based on the active functional component, if the molar amount of the supported catalyst is less than 1% of the molar amount of sucrose, the amount is too small, resulting in a large amount of sucrose remaining in the reactant cannot participate in the reaction, which is not conducive to the forward reaction. If the molar amount of the supported catalyst is more than 200% of the molar amount of sucrose, the amount is too much, which may cause the occurrence of a diester or multi-esterification reaction and produce a large number of by-products.

Type and Amount of the Low-Alcohol Carboxylate

In some embodiments of the present disclosure, in the method, there is no limitation on the type of the low-alcohol carboxylate, may be, but is not limited to, one or more selected from the group consisting of methyl esters, ethyl esters, propyl esters, isopropyl esters, n-butyl esters, isobutyl esters, tert-butyl esters, and phenylmethyl esters of stearic acid, benzoic acid, acetic acid, butyric acid, and lauric acid. In some other embodiments, the low-alcohol carboxylate may be one or more selected from the group consisting of methyl stearate, ethyl acetate, and methyl benzoate.

In some embodiments of the present disclosure, there is no limitation on the amount of the low-alcohol carboxylate. A volume of the low-alcohol carboxylate is less than 30% of the volume of the polar aprotic solvent. In some embodiments, the volume of the low-alcohol carboxylate is less than 20% of the volume of the polar aprotic solvent. In some other embodiments, the volume of the low-alcohol carboxylate is less than 15% of the volume of the polar aprotic solvent. If the volume of the low-alcohol carboxylate is more than 30% of the volume of the polar aprotic solvent, it will cause unnecessary waste and cannot provide any other beneficial effects.

Dehydration and Dealcoholization Treatment

In the present disclosure, the dehydration and dealcoholization treatment may be achieved by the existing technologies such as vacuum distillation or may be achieved by the method recommended in the embodiment. During the transesterification reaction process of the present disclosure, the polar aprotic solvent or low-alcohol carboxylate is added at an excessive amount to the reaction mixture, and then the purpose of dehydration and dealcoholization is realized by distilling the excessive polar aprotic solvent or low-alcohol carboxylate. Because water or low alcohol (a by-product) will be dissolved or entrained in the polar aprotic solvent or low-alcohol carboxylate, during the distillation of the two, water or low alcohol will be taken away from the reaction system to achieve the purpose of separating water and low alcohol.

In some embodiments of the present disclosure, there is no limitation on the conditions of the dehydration and dealcoholization. In some other embodiments, the conditions of the distillation may be, but are not limit to: the distillation is conducted at a temperature of 40° C. to 100° C. under a pressure of 0.01 kPa to 100 kPa for 1 min to 12 h. In some other embodiments, the distillation is conducted at a temperature of 60° C. to 80° C. under a pressure of 0.5 kPa to 90 kPa for 30 min to 4 h.

If the distillation temperature is lower than 40° C., the distillation pressure is more than 100 kPa, and the distillation time is shorter than 1 min, the water and low alcohol generated by the transesterification reaction cannot be completely separated, the distillation speed is too low, the distillation degree is not thorough enough, and the separation effect is poor. If the distillation temperature is higher than 100° C., the distillation pressure is less than 0.01 kPa, and the distillation time is longer than 12 h, the distillation speed is too fast, the reaction process cannot be well controlled, and the target product is easily distilled out with evaporants, resulting in decreased yield.

The sucrose-6-ester synthesized in the present disclosure are different according to the type of the low-alcohol carboxylate, and can be used as a food additive, a chemical product, or a synthesis intermediate for other reactions. For example, sucrose-6-acetate and sucrose-6-benzoate can be used as intermediates for the synthesis of a sweetener sucralose.

Testing Methods Involved in the Present Disclosure

In each example and comparative example in the present disclosure, the content or purity of each substance (including sucrose, sucrose-6-esters, or the like) is measured by high-performance liquid chromatography (HPLC) under the following conditions, which will not be repeated in each example.

Analytical determination conditions of HPLC: High-performance liquid chromatograph of Shimadzu, Japan: RID-10A differential refractive index detection, LC-10ADVP high-pressure pump, and CTO-10ASVP incubator; chromatographic column: Agilent XDB C18 column (250 mm×4.6 mm, 5 μm); mobile phase: methanol-0.125% dipotassium phosphate (DKP) aqueous solution (4:6); column temperature: 30° C.; and flow rate: 1.0 mL/min. Methanol (chromatographically pure), DKP (analytically pure), ultra-pure water (UPW), and standards are required, The content is determined by an external standard method.

Normalization means that when a mixture is separated and assayed by HPLC, the amount of all substances is artificially specified to be 100%, and the percentage of each substance to all substances is determined according to the peak area.

Moisture Test Method

The moisture content is determined by the Karl Fischer method or the moisture content tester, which can refer to the prior art and will not be repeated in each example.

EXAMPLE 1

A surface of white carbon black with an SSA of 200 $m^2/g$ to 450 $m^2/g$ was subjected to a coupling treatment with γ-trimethoxysilyldodecylbutyltin oxide, obtaining a supported catalyst C1.

According to a ratio of 1,000 Kg of sucrose, 2,000 Kg of the supported catalyst C1, and 10 $m^3$ of DMF, a suspension reaction solution was prepared. The suspended reaction solution was heated to 80° C. and dissolved, obtaining a solution. Then 2 $m^3$ of methyl acetate was added to the solution, obtaining a suspension.

A bubble-cap tower reactor was used for a transesterification reaction, wherein the bubble-cap tower had a diameter of 50 cm, a bubble-cap size of 30×8 mm, and 20 plates. The residence time was about 30 min. The transesterification reaction was conducted at 60° C. After the reaction, a suspension mainly composed of sucrose-6-acetate was obtained.

The mixture mainly composed of sucrose-6-acetate was directly filtered to recover the supported catalyst, obtaining a sucrose-6-acetate mother liquor. The obtained supported catalyst was washed with a small amount of solvent for later reuse.

The sucrose-6-acetate mother liquor obtained was about 11 $m^3$. The content of sugar compounds was calculated to be about 10%. According to HPLC analysis, the products were as follows:

a. sucrose-6-acetate: 10.33% (89.9%, normalized);
b. diacetate: 0.99% (8.7%, normalized); and
c. sucrose: 0.04% (0.23%, normalized).

EXAMPLE 2

A surface of white carbon black with an SSA of 200 $m^2/g$ to 450 $m^2/g$ was subjected to an activation treatment with γ-aminotrimethoxysilane, and then subjected to a coupling treatment with γ-chlorohexyldibutyltin oxide, obtaining a supported catalyst C2.

The prepared supported catalyst C2 was added to 70 g of sucrose and 300 mL of DMF. The resulting solution was heated to 80° C., obtaining a sucrose solution.

Ethyl acetate was continuously added to allow a transesterification reaction under negative-pressure distillation. The reaction condition we as follows: a negative pressure was 95 kPa, a reaction temperature was 70° C., and ethyl acetate was continuously supplemented until the alcohol content in the distilled ethyl acetate reached below 100 ppm. The transesterification reaction was conducted for about 2 h, obtaining a suspension mainly composed of sucrose-6-acetate.

The obtained suspension was filtered to obtain the catalyst and a sucrose-6-acetate mother liquor. The catalyst was recovered and washed with a small amount of solvent for later reuse.

The content of sugar compounds contained in the sucrose-6-acetate mother liquor was calculated to be about 20%. According to HPLC analysis, the products were as follows:

a. sucrose-6-acetate: 17.5% (89.6%, normalized);
b. diacetate: 1.68% (8.3%, normalized); and
c. sucrose: 0.05% (0.25%, normalized).

EXAMPLE 3

A surface of aluminum oxide with an SSA of 100 $m^2/g$ to 250 $m^2/g$ was subjected to a coupling treatment with γ-phosphate hexyldibutyltin oxide, obtaining a supported catalyst C3.

The prepared supported catalyst C3 was added to 70 g of sucrose and 300 mL of DMF. The resulting solution was heated to 80° C., obtaining a sucrose solution.

Ethyl stearate was continuously added to allow a transesterification reaction under a negative pressure. The reaction condition we as follows: a negative pressure was 95 kPa, a reaction temperature was 65° C., and anhydrous DMF was continuously supplemented until the alcohol content in distilled DMF was below 100 ppm. The transesterification reaction was conducted for about 4 h, obtaining a suspension mainly composed of sucrose-6-acetate.

The obtained suspension was directly filtered to obtain the catalyst and a sucrose-6-acetate mother liquor. The catalyst was recovered and washed with a small amount of solvent for later reuse.

The content of sugar compounds contained in the sucrose-6-acetate mother liquor was calculated to be about 20%. According to HPLC analysis, the products were as follows:

a. sucrose-6-stearate: 17.93% (90.6%, normalized);
b. distearate: 1.52% (7.7%, normalized); and
c. sucrose: 0.04% (0.23%, normalized).

EXAMPLE 4

A surface of white carbon black with an SSA of 200 $m^2/g$ to 450 $m^2/g$ was subjected to an activation treatment with γ-mercaptotrimethoxysilane, and then subjected to a coupling treatment with γ-chlorohexyldibutyltin oxide, obtaining a supported catalyst C4.

A 1,000 mL four-necked round-bottomed flask equipped with a mechanical stirrer, a thermometer, and a condenser pipe including a water separator was taken. 150 g of sucrose and 600 mL of DMF were added. The resulting mixture was heated to 90° C. until the sucrose was completely dissolved and then cooled to 60° C. 120 g of the supported catalyst C4 and 150 mL of methyl laurate were added. The resulting mixture was heated to 90° C., and distilled under negative pressure to promote a transesterification reaction for about 5 h. After the reaction was completed, the resulting system was cooled to room temperature and filtered, obtaining the catalyst. The catalyst was recovered, obtaining a sucrose-6-laurate mother liquor. According to HPLC analysis, the products were as follows:

a. sucrose-6-laurate: 19.05% (86.5%, normalized);
b. dilaurate: 2.43% (11.0%, normalized); and
c. sucrose: 0.09% (0.36%, normalized).

Comparative Example 1

Macroporous activated carbon with an SSA of about 1,000 $m^2/g$ was taken. The surface of the macroporous activated carbon was modified into a hydrophilic surface through an activation treatment with hydrogen peroxide. A titanium dioxide layer of about 10 nm was coated by the tetrabutyl titanate (TBT) method on the surface of the modified activated carbon. The coated activated carbon was centrifuged, washed, and dried for later use. The γ-hydroxytrimethoxysilane was modified on the surface of the activated carbon coated with titanium dioxide. After the hydroxyl modification was completed, the surface of the macroporous activated carbon was coupled with γ-chlorohexyldibutyltin oxide, obtaining a supported catalyst C5.

The supported catalyst C5 was added to 70 g of sucrose and 300 mL of DMF. The resulting solution was heated to 80° C., obtaining a sucrose solution.

A transesterification reaction was conducted for about 4 h under a negative pressure in a conventional reactor, obtaining a suspension mainly composed of sucrose-6-acetate. The reaction conditions were as follows: a negative pressure was 95 kPa, a temperature was 75° C., and anhydrous DMF was continuously supplemented until a water content in distilled DMF was below 100 ppm.

The sugar compounds content in the suspension obtained was calculated to be about 20%. Cyclohexane was added to the suspension at a ratio of 1:2. Acetic anhydride was added dropwise to the suspension according to a ratio of 1.1:1 at a temperature below 10° C., and the resulting mixture was subjected to an acylation reaction. After the acylation reaction continued at a temperature below 10° C. for 2 h, a quenching reaction was conducted with water at a ratio of 0.05:1. The resulting reaction system was centrifuged, obtaining a supported catalyst and a sucrose-6-acetate mother liquor. The supported catalyst was washed and recovered. The sucrose-6-acetate mother liquor had a water content of about 5%, and thus must undergo dehydration before being used subsequently. According to HPLC analysis, the products were as follows:

a. sucrose-6-acetate: 16.264% (85.6%, normalized);
b. diacetate: 2.337% (12.3%, normalized); and
c. sucrose: 0.06% (0.31%, normalized).

Comparative Example 2

According to the mass ratio of sucrose, an organic tin esterification accelerator (1,1,3-diacetoxy-1,1,3,3-tetrabutyldistannoxane), and a polar aprotic solvent (DMF) of 1:2:10 were taken to prepare into 300 kg of a reaction solution. The reaction solution was heated at 90° C. and dissolved, obtaining a reaction mixed solution.

The reaction mixed solution was dehydrated in a packed tower. The packed tower had a diameter of 40 mm and was packed with a 3×8 glass spring packing at a packing height of 1 m, which was equivalent to 10-stage tower plates.

The reaction mixed solution prepared above was fed from an inlet at the top of the packed tower. The negative pressure was kept at 0.5 kPa, At the same time, a cyclohexane vapor (100° C., 4 atm) was fed from a flask gas inlet at the bottom of the packed tower. The reaction mixed solution reacted with the cyclohexane vapor in countercurrent contact. The distillate (a vapor including cyclohexane, water, and DMF) discharged from the top of the packed tower was condensed and collected, and could be recycled after drying and anhydrous treatment.

The liquid sample was collected in a flask at the bottom of the packed tower. The obtained product was transparent and light-amber. The retention time of the reaction solution in the gas-liquid exchange reactor was about 1 min.

The sucrose content in the solution obtained was calculated to be 10%. The resulting solution was pressed into another reactor. Acetic anhydride was added dropwise to the solution in a mass ratio of sucrose to acetic anhydride being 1:1.1 at a temperature below 10° C., and the resulting mixture was subjected to an acylation reaction. After the acylation reaction continued at a temperature below 10° C. for 2 h, a quenching reaction was conducted with water at 0.25:1. The organo-tin compound was extracted with cyclohexane at a ratio of 1:1. The resulting sucrose-6-acetate solution was analyzed by HPLC. The analysis results of the products were as follows:

a. sucrose-6-acetate: 7.56% (72.05%, normalized);
b. diacetate: 0.46% (4.36%, normalized); and
c. sucrose: 2.39% (22.76%, normalized).

It can be seen from Examples 1 to 4 and Comparative Example 1 that, when the catalyst provided in the present disclosure is used to catalyze the reaction between sucrose and a low-alcohol carboxylate, the selectivity for the sucrose-6-ester can be significantly improved. In Examples 1 to 4, the highest yield of the sucrose-6-acid can reach 17.93% (90.6%, normalized), but is only 16.264% (85.6%, normalized) in Comparative Example 1.

It can be seen from Examples 1 to 4 and Comparative Example 2 that, compared with the mono-group protection method used in Comparative Example 2, the method provided in the present disclosure results in a high yield for the sucrose-6-carboxylate, a low occurrence probability of side reaction, and exhibits complete sucrose reaction. It can be seen from the yield of sucrose-6-acetate, in some examples of the present disclosure, the yield can reach 17.93% (90.6%, normalized), while in Comparative Example 1, the yield of sucrose-6-acetate is only 7.56% (72.05%, normalized); that is, the yield of the sucrose-6-carboxylate in the present disclosure is significantly higher than that in the prior art. Similarly, it can be seen from the contents of diacetate and sucrose in the reaction products that in the present disclosure, the occurrence probability of side reaction is significantly reduced, and the conversion of sucrose is more thorough.

In summary, the present disclosure provides a supported catalyst, wherein an active component of an organic tin compound shown in formula (1) is supported on an inorganic carrier to obtain the supported catalyst. The supported catalyst can highly selectively catalyze a transesterification reaction between sucrose and a low-alcohol carboxylate to obtain a sucrose-6-ester. After the reaction is completed, the supported catalyst can be recovered almost completely through filtration with almost no loss. In this way, there is no need to add a new catalyst for the next production run, and there is no entrained catalyst in the product, such that the subsequent reaction will not be adversely affected. The use of the low-alcohol carboxylate as the reaction raw material can avoid the control restrictions on the use of carboxylic anhydride in the prior art, and can also avoid recovering the catalyst after the quenching of the residual acylating agent with water and the subsequent complex dehydration processes, which makes the overall process simple and easy to implement and has significant economic benefits in terms of manpower, equipment, and energy consumption.

The above are merely specific embodiments of the present disclosure. Under the above teaching of the present disclosure, those skilled in the art may make other improvements or variations based the above examples. It should be understood by those skilled in the art that the above detailed description is merely intended to better explain the purpose of the present disclosure, and the protection scope of the present disclosure shall be subject to the protection scope of the claims.

In addition, those skilled in the art can understand that although some embodiments described herein include some features included in other embodiments but not others, the combination of features of different embodiments is meant to fall within the scope of the present disclosure and to form different embodiments. For example, in the following claims, any one of the claimed embodiments can be used in any combination.

What is claimed is:

1. A supported catalyst for catalyzing a transesterification reaction between sucrose and carboxylate, comprising an active functional component and an inorganic carrier, wherein the active functional component is a compound shown in formula (1):

formula (1)

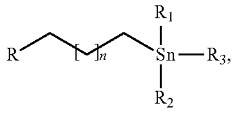

wherein n is a natural number greater than or equal to 2;
R is an atom linked to a surface of the inorganic carrier; and one or two of $R_1$, $R_2$, and $R_3$ is/are hydrocarbyl, and the rest each are independently any one selected from the group consisting of oxygen, hydroxyl, hydrocarbyloxy, and acetoxy.

2. The supported catalyst according to claim 1, wherein R is any one selected from the group consisting of silicon, oxygen, nitrogen, sulfur, and phosphorus.

3. The supported catalyst according to claim 2, wherein the active functional component accounts for 1 ppm to 40% of a weight of the inorganic carrier.

4. The supported catalyst according to claim 1, wherein hydrocarbyl is selected from the group consisting of alkyl, cycloalkyl, aryl, and aralkyl.

5. The supported catalyst according to claim 4, wherein the active functional component accounts for 1 ppm to 40% of a weight of the inorganic carrier.

6. The supported catalyst according to claim 1, wherein the hydrocarbyloxy is selected from the group consisting of alkoxy and phenoxy.

7. The supported catalyst according to claim 6, wherein the active functional component accounts for 1 ppm to 40% of a weight of the inorganic carrier.

8. The supported catalyst according to claim 1, wherein the inorganic carrier is one or a mixture of two or more selected from the group consisting of silicon dioxide, titanium dioxide, activated carbon, and aluminum oxide.

9. The supported catalyst according to claim 8, wherein the active functional component accounts for 1 ppm to 40% of a weight of the inorganic carrier.

10. The supported catalyst according to claim 1, wherein the inorganic carrier has a specific surface area (SSA) of greater than 10 $m^2/g$.

11. The supported catalyst according to claim 1, wherein the active functional component accounts for 1 ppm to 40% of a weight of the inorganic carrier.

12. A method for synthesizing a sucrose-6-ester, comprising: using the supported catalyst according to claim 1 to catalyze a transesterification reaction between sucrose and a low-alcohol carboxylate to obtain the sucrose-6-ester.

13. The method according to claim 12, comprising:
sucrose dissolution: heating and dissolving sucrose in a polar aprotic solvent to obtain a sucrose solution;
catalyst addition: adding the supported catalyst according to claim 1 into the sucrose solution to obtain a reaction suspension; and
transesterification reaction: adding a low-alcohol carboxylate to the reaction suspension, and conducting a dehydration and dealcoholization treatment to promote a transesterification reaction to obtain a reaction mixed solution having the sucrose-6-ester as a main product.

14. The method according to claim 13, further comprising:
post-treatment: filtering the reaction mixed solution to separate the supported catalyst to obtain a sucrose-6-ester mother liquor.

15. The method according to claim 13, wherein the low-alcohol carboxylate is one or more selected from the group consisting of methyl esters, ethyl esters, propyl esters, isopropyl esters, n-butyl esters, isobutyl esters, tert-butyl esters, and phenylmethyl esters of stearic acid, benzoic acid, acetic acid, butyric acid, and lauric acid.

16. The method according to claim 13, wherein the polar aprotic solvent is one or more selected from the group consisting of dimethyl sulfoxide (DMSO), acetonitrile, 1,4-dioxane, methyl ethyl ketone (MEK), methyl isobutyl ketone (MIBK), nitromethane, nitroethane, cyclohexanone, N-methylpyrrolidone (NMP), NMP, N,N-dimethylacetamide (DMA), hexamethylphosphoramide (HMPA), and N,N-dimethylformamide (DMF).

17. The method according to claim 13, wherein a ratio of a volume of the polar aprotic solvent to a mass of sucrose is in a range of 2-50 mg/L;
based on the active functional component, a molar ratio of the supported catalyst to the sucrose is in a range of 0.01-2; and
a volume of the low-alcohol carboxylate is less than 30% of the volume of the polar aprotic solvent.

18. The method according to claim 13, wherein the dehydration and dealcoholization treatment is conducted by distillation of an additional polar aprotic solvent or low-alcohol carboxylate added to the reaction suspension.

19. The method according to claim 18, wherein the distillation is conducted at a temperature of 40° C. to 100° C.; the distillation is conducted under a pressure of 0.01 kPa to 100 kPa; and the distillation is conducted for 1 min to 12 h.

20. The method according to claim 13, wherein the transesterification reaction is conducted in a kettle-type reactor or a continuous countercurrent reaction distillation tower.

* * * * *